(12) United States Patent
Kubota et al.

(10) Patent No.: US 9,491,933 B2
(45) Date of Patent: Nov. 15, 2016

(54) INFECTED NAIL OF ANIMAL INFECTED WITH FUNGUS

(75) Inventors: Nobuo Kubota, Kanagawa (JP); Tsuyoshi Shimamura, Kanagawa (JP); Saori Nagasaka, Kanagawa (JP)

(73) Assignee: POLA PHARMA, INC., Tokyo (JP)

( * ) Notice: Subject to any disclaimer, the term of this patent is extended or adjusted under 35 U.S.C. 154(b) by 55 days.

(21) Appl. No.: 12/810,202

(22) PCT Filed: Dec. 25, 2008

(86) PCT No.: PCT/JP2008/073565
§ 371 (c)(1),
(2), (4) Date: Jun. 23, 2010

(87) PCT Pub. No.: WO2009/081977
PCT Pub. Date: Jul. 2, 2009

(65) Prior Publication Data
US 2010/0275277 A1  Oct. 28, 2010

(30) Foreign Application Priority Data

Dec. 25, 2007 (JP) ................................ 2007-331818
Dec. 25, 2007 (JP) ................................ 2007-331832

(51) Int. Cl.
| | | |
|---|---|---|
| A61K 48/00 | (2006.01) | |
| A01K 67/00 | (2006.01) | |
| C12Q 1/02 | (2006.01) | |
| C12Q 1/18 | (2006.01) | |

(52) U.S. Cl.
CPC .............. *A01K 67/00* (2013.01); *C12Q 1/025* (2013.01); *C12Q 1/18* (2013.01); *A01K 2207/10* (2013.01); *A01K 2227/107* (2013.01); *A01K 2267/0337* (2013.01)

(58) Field of Classification Search
CPC ............. A01K 67/00; A01K 2207/10; A01K 2267/0337
See application file for complete search history.

(56) References Cited

U.S. PATENT DOCUMENTS

| | | | |
|---|---|---|---|
| 7,374,772 B2* | 5/2008 | Bommarito | 424/404 |
| 2004/0001791 A1* | 1/2004 | Zeiler | 424/61 |
| 2004/0072807 A1* | 4/2004 | Gibson et al. | 514/169 |
| 2004/0091506 A1* | 5/2004 | Bommarito | 424/400 |
| 2007/0082375 A1 | 4/2007 | Tatsumi et al. | |
| 2008/0003636 A1 | 1/2008 | Tatsumi et al. | |

FOREIGN PATENT DOCUMENTS

| | | |
|---|---|---|
| JP | 2001-128696 | 5/2001 |
| JP | 2001-133449 | 5/2001 |
| JP | 2002-65695 | 3/2002 |
| JP | 2003-506101 | 2/2003 |
| WO | WO 01/07643 A1 | 2/2001 |
| WO | WO 01/11953 A1 | 2/2001 |
| WO | WO 2009/081976 A1 | 7/2009 |

OTHER PUBLICATIONS

Rashid et al. Br J Dermatol 133(6):932-940, 1995; abstract.*
Lestschenko et al. Mykosen 25(5): abstract only, 1985.*
Zlotnik et al. Br. J. Exp. Path. 52:395-407, 1971.*
Majima et al., A novel mycological anallysis valuable for evaluating therapeutic efficacy of antimycotics against experimental dermatophytosis in guinea pigs. Mycoses. 2005; 48:108-113.
Omuta et al., Histopathological study of experimental endophthalmitis induced by bloodstream infection with Candida albicans. Jpn J Infect Dis. 2007; 60: 33-39.
Shimamura et al., P-089 Tsume Hakusen Dobutsu Model Sakusei ni Kansuru Kento. [Histopathological investigation of producing animal model of ringworm of the nails]. Jpn J Med Mycology. 2008; 49: 98.
Suzuki et al., P-0555 Tsume Hakusen Dobutsu Model ni Okeru Byori Soshikigakuteki Kento. [Histopathological investigation using animal model of ringworm of the nails]. Jpn J Med. Mycology 2008; 49: 89.
Tatsumi et al., Therapeutic efficacy of topically applied KP-103 against experimental tinea unguium in guinea pigs in comparison with amorolfine and terbinafine. Antimicrobial Agents and Chemotherapy, 2002; 46(12): 3797-3801.
Uchida et al., Achievement of complete mycological cure by topical antifungal agent NND-502 in guinea pig model of tinea pedis. Microbiol Immunol. 2003: 47(2): 143-146.
Nakashima et al., Experimental tinea unguium model to assess topical antifungal agents using the infected human nail with dermatophyte in vitro. J Infect Chemother. Dec. 2002;8(4):331-5.

\* cited by examiner

*Primary Examiner* — Marcia S Noble
(74) *Attorney, Agent, or Firm* — Wolf, Greenfield & Sacks, P.C.

(57) ABSTRACT

The invention can produce an infected nail of an animal and an infected animal model in which the nail plate and nail bed of the nail are sufficiently infected with a superficial fungus which were difficult to be produced in the past, and provides an evaluation method useful for development of a therapeutic agent for intractable infectious diseases such as tinea unguium using the nail and the infected animal model. For producing the infected nail of an animal and the infected animal model infected with a superficial fungus, an immunosuppressive component is administered to an animal in advance to decrease immunocompetence, and then, a superficial fungus is inoculated into the animal, whereby the infected nail of an animal and the infected animal model reflecting clinical manifestation in which the nail plate and nail bed of the nail are sufficiently infected with the superficial fungus can be produced with good reproducibility in a short period of time.

5 Claims, 5 Drawing Sheets

BEFORE INFECTION          AFTER INFECTION

INFECTED NAIL OF ANIMAL INFECTED WITH FUNGUS

RELATED APPLICATION

This application is a national stage filing under 35 U.S.C. §371 of international application PCT/JP2008/073565, filed Dec. 25, 2008, the disclosure of which is incorporated herein by reference.

TECHNICAL FIELD

The present invention relates to an infected nail of an animal infected with a fungus, an infected animal model having the nail, and a method for evaluation of a drug for the treatment of an infectious disease employing the nail or the infected animal model.

BACKGROUND ART

In recent years, as aging has progressed, problems of infectious disease in elderly people with deterioration in bodily functions such as immunocompetence have been attracting attention. As one example, fungal nail disease, for which a superficial fungus is the causative microorganism, can be cited. This is a fungal disease that is caused by propagation in the nail of a fungus such as *Trichophyton mentagrophytes* that normally causes a fungal disease in the skin. In such a fungal nail disease, since the nail is a hard tissue formed from keratin, it is difficult for an antifungal agent or a composition containing an antifungal agent used for a cutaneous fungal disease to be absorbed in the nail, and there are many problems in treatment involving administering a drug via the nail. Because of this, in the current situation it is difficult to develop a drug useful for onychomycosis, and as one contributory factor the absence of a suitable animal model for onychomycosis can be cited.

For example, as an infected animal model for evaluating the effect of an antifungal agent toward onychomycosis, a method in which a nail of a guinea pig is damaged by abrading with sandpaper, etc. and this is closed-patched with a dispersion of fungal arthroconidia (Patent Document 1), etc, is known, but in such a method the fungus is attached only to the surface of the nail, and although the fungus is present on the nail, it is difficult to say that onychomycosis, which is accompanied by degeneration in the interior of the nail and inhibits distribution of a drug, is reproduced. In such a model, since the fungus is present only on the nail surface, no cloudy part is formed in the nail, the area within the nail in which the fungus grows and is distributed is very small, and it is not an onychomycosis model in which the fungus has infiltrated into a deep part of the nail.

Other than the above, there are several reports relating to methods for infecting an animal with a fungus (Non-Patent Documents 1 to 3), but the period taken for infection is 60 days or longer, which is very long; moreover, the infection intensity is low and the fungus does not infiltrate sufficiently into a deep part of the nail, and this is not satisfactory in terms of producing an infection model that reflects the clinical manifestation with good reproducibility. It is thought that this is due to the structure of the nail and selection characteristics of the *Trichophyton* host and infestation site, but such onychomycosis and infected animal models cannot sufficiently function as evaluation systems for an antifungal agent. Furthermore, there are several problems with fungal nail disease as described above, and in spite of there being problems with the evaluation period and the reproducibility, there has been hardly any investigation into an infected animal model in order to solve the problems.

On the other hand, as a method for preparing an infected animal model, a method for infecting an animal with a fungus after compromising the immunity of the animal by administration of a steroid so as to put it in an easily infected state has been reported (Non-Patent Document 4), but it is clear that infection is affected by compromising the immunity, it is limited to an infected animal model in which infection is caused in the eyeball or mucosal tissue around the eye, where establishment of infection is very easy, and there are no examples of it being applied to the nail.

As hereinbefore described, the current situation is that neither an evaluation model appropriate for onychomycosis, etc. nor an accurate evaluation method therefor has yet been established.

Patent Document 1: International Patent Application WO 2001/7643
Patent Document 2: JP, A, 2001-128696
Patent Document 3: JP, A, 2002-65695
Patent Document 4: JP, A, 2001-133449
Non-Patent Document 1: Antimicrobial agents and chemotherapy, 46 (12), p. 3797-3801 (2002)
Non-Patent Document 2: Microbiol. Immunol., 47 (2), p 143-146 (2003)
Non-Patent Document 3: Mycoses, 48, p 108-113 (2004)
Non-Patent Document 4: Jpn. J. Infect Dis., 60, p. 33-39 (2007)

DISCLOSURE OF INVENTION

Problems to be Solved by the Invention

It is therefore an object of the present invention to prepare an infected nail of an animal infected sufficiently with a fungus and an infected animal model having the nail that are able to be applied to full evaluation of an antifungal agent, and to provide an evaluation method, employing the nail or the infected animal model, useful for development of a drug for the treatment of an intractable infectious disease such as onychomycosis.

Means for Solving the Problems

In order to evaluate the clinical effect of an antifungal agent, an intensive investigation into an infected nail as a model for clinically observed onychomycosis has been carried out by the present inventors; it has been found that when, after the immunocompetence of an animal is compromised in advance by immunocompromising means, the nail is infected by inoculation with a fungus and then subjected to PAS staining, surprisingly an infected animal nail and an infected animal model that approximate to human onychomycosis in which the infection intensity is outstandingly higher than conventional evaluation models and the fungus has infiltrated into a deep part of the nail can be prepared with good reproducibility, and as a result of further research the present invention has been accomplished.

That is, the present invention relates to an infected nail of an animal infected with a fungus, wherein when PAS staining is carried out a stained portion is at least 4% of the cross-sectional area of the nail.

Furthermore, it relates to the infected nail wherein the stained portion is present more in the lower half in the nail depth direction than in the upper half.

Moreover, it relates to the infected nail wherein the fungus is a *Trichophyton*.

Furthermore, it relates to the infected nail wherein the *Trichophyton* is *Trichophyton mentagrophytes*.

Moreover, it relates to the infected nail wherein the animal is one or more types selected from rabbit, guinea pig, rat, dog, and monkey.

Furthermore, it relates to the infected nail wherein it is used for evaluation of a drug for the treatment of onychomycosis.

Moreover, it relates to an infected animal model having the infected nail.

Furthermore, it relates to a method for evaluating a drug for the treatment of onychomycosis, the method employing the infected nail or the infected animal model.

Effects of the Invention

The present invention enables there to be provided with good reproducibility an infected nail of an animal and an infected animal model that reflect clinical manifestation and in which a nail plate and a nail bed of a nail, where it is difficult to establish an infection, are infected sufficiently with a fungus.

With regard to the infected nail of an animal of the present invention, since the fungus infiltrates deeply into the nail it becomes a model for clinically observed onychomycosis, and it can establish, as an evaluation model for development of an antifungal agent, an accurate evaluation system that is useful for development of a drug for the treatment of an intractable infectious disease such as onychomycosis, which is conventionally impossible.

BEST MODE FOR CARRYING OUT THE INVENTION

With regard to a fungus with which the nail of an animal of the present invention is infected, a fungus of a disease for which the effect of treatment by a drug after infection is low is preferable; examples thereof include a superficial fungus and a deep-seated fungus, and when a disease of the nail is anticipated, a superficial fungus is more preferable. Examples of the superficial fungus include those selected from *Trichophyton mentagrophytes, Trichophyton rubrum, Trichophyton violaceum, Trichophyton verrucosum, Trichophyton tonsurans, Microsporum canis, Microsporum gypseum, Epidermophyton floccosum, Hortaea werneckii, Alternaria alternata, Aspergillus fumigatus, Aspergillus flavus, Aspergillus terreus, Paecilomyces lilacinus, Fusarium solani, Scopulariopsis brevicaulis, Candida albicans, Candida tropicalis, Candida parapsilosis, Candida glabrata, Cryptococcus neoformans*, and *Trichosporon asahii*; for evaluation of onychomycosis, the *Trichophyton* genus, which is promising as a causative fungus, is preferable, and when ease of formation of conidia such as germinating conidia, arthroconidia, or microconidia, in particular arthroconidia or microconidia, is taken into consideration, *Trichophyton mentagrophytes* is more preferable.

As the mode of the fungus for infection, fungal cells, mycelia, spores, germinating conidia, arthroconidia, microconidia, etc. can be cited; from the viewpoint of susceptibility to local infection, germinating conidia, arthroconidia, and microconidia are preferable, and from the viewpoint of collection of conidia, counting of the number of fungal cells, and ease of inoculation, arthroconidia and microconidia are more preferable.

The nail of an animal of the present invention is a plate-shaped tissue consisting of hard keratin present on the back of a finger/toe tip of an animal hand or foot, the upper half, in the depth direction, of the nail being called the nail plate side of the nail and the lower half being called the nail bed side of the nail. Furthermore, when the nail is equally divided into three from the extremity in the longer diameter direction, the divisions are called the nail extremity side, the nail middle part, and the nail matrix side of the nail.

In the present invention, after the nail is infected by inoculating it with a fungus, PAS staining, which is described later, is carried out, and the proportion of a stained portion area relative to the cross-sectional area of the nail, that is, the proportion of the area occupied by fungal cells, is calculated as a percentage. From the viewpoint of an evaluation model that reflects the clinical manifestation of human onychomycosis, etc., the stained portion area relative to the cross-sectional area of the nail is preferably 4% or greater, more preferably 4.5% or greater, yet more preferably 5% or greater, and particularly preferably 6% or greater. When the proportion of the stained portion area relative to the cross-sectional area of the nail is less than 4%, that is, when the proportion of the area occupied by fungal cells is less than 4%, accurate analysis of fungal infection in the nail becomes difficult.

Furthermore, in terms of the model being one that is similar to one classified as onychomycosis in clinical practice, one in which more stained portion is present in the lower half, in the depth direction, of the nail than in the upper half, that is, one in which more fungus is distributed on the nail bed side than on the nail plate side, is preferable.

Similarly, in terms of the model being one that is similar to one classified as onychomycosis in clinical practice, one in which stained portions are present in all of the nail extremity side, the nail middle part, and the nail matrix side of the nail when the nail is equally divided into three in the longer diameter direction, that is, one in which fungus is distributed in all parts of the nail, is preferable. Moreover, one in which more stained portion is present in a specific site such as the extremity side or the nail matrix side, that is, one in which more fungus is distributed in a specific site such as the nail extremity side or the nail matrix side, is also preferable since this can reflect the clinical manifestation in some cases.

Localization of fungus in the nail in onychomycosis is diverse, and includes the distal subungual type (type in which infection starts from the nail extremity), the proximal subungual type (type in which infection starts from the nail epithelium (cuticle) side), the superficial type (type in which infection occurs in a shallow portion on the nail plate side), and the full thickness type (type in which infection occurs in the whole area of the nail); in accordance with the present invention, it becomes possible to prepare an infection model in which the fungus has infiltrated sufficiently into the nail bed side of a deep part of the nail and the entire nail is infected with the fungus or an infection model in which a specific site such as the extremity side or the nail matrix side is infected more with the fungus, and it becomes possible for the first time to prepare an infected animal model for onychomycosis that reflects clinical manifestations such as the full thickness type, the distal subungual type, and the proximal subungual type.

As the animal used in preparation of the present invention, an animal for which a nail as a target can be coated with a fungus is used, and examples thereof include established experimental animal species such as rodents such as mouse, rat, guinea pig, hamster, or rabbit, Canidae such as dog, Felidae such as cat, livestock such as sheep, goat, or cattle, and primates (but excluding humans) such as *Cercopithecus aethiops, Macaca fascicularis*, and night monkey; in terms of genetic homogeneity, availability, and handling preferred examples include mouse, rat, guinea pig, rabbit, dog, and monkey, in terms of ease of use more preferred examples include guinea pig and rabbit, and as a model for onychomycosis rabbit is yet more preferable since an infected site is large. With regard to the gender of such an animal, either female or male may be used. This is because there is no difference in terms of gender for the nail or the infection of the nail with a fungus.

The infected nail of an animal and the infected animal model of the present invention may be obtained by compromising the immunity of an animal by immunocompromising means and then carrying out infection by inoculating the nail and/or the skin around the nail with a superficial fungus.

Preferred examples of the immunocompromising means for compromising the immunity of an animal include administration of an immunosuppressive agent, local restriction of bloodstream, restriction of nutritional intake, application of radiation, and infection with a virus that causes immunodeficiency; in terms of simplicity of operation and adjustment of immunocompromise more preferred examples include administration of an immunosuppressive agent and local restriction of bloodstream, and administration of an immunosuppressive agent is particularly preferable.

As an indicator for determining immunocompromise, examples include the degree of decrease in weight following a transient increase after administration of an immunosuppressive agent, a change in the count of various blood cell components such as lymphoid cells, a change in CD4/CD8 ratio, and a change in the amount of various cytokines involved in the immune mechanism, and in terms of reproducibility and the indicator being independent of the animal species preferred examples include the degree of decrease in weight following a transient increase after administration of an immunosuppressive agent. The mechanism of action of the change in weight after administration of an immunosuppressive agent is complicated and is not necessarily clear, but this is a species-independent phenomenon that is observed in many animals, and can be used as an indirect indicator for expression of a pharmacological effect of an immunosuppressive agent.

From the viewpoint of sufficient immunocompromise and prevention of excessive debilitation of an animal, it is necessary to cautiously carry out determination of immunocompromise while examining the effects on the animal that accompany immunocompromise, such as food intake by the animal. Typically, it is determined that the degree of immunocompromise is desirable for inoculation with an infecting microorganism when the degree of decrease in weight following a transient increase after administration of an immunosuppressive agent is preferably in the range of decrease of 1% to 30% from the weight prior to administration and, taking into consideration sufficient immunocompromise and prevention of excessive debilitation of an animal, it is more preferably a decrease of 3% to 30%, yet more preferably a decrease of 5% to 30%, and particularly preferably a decrease of 5% to 20%.

In addition, when a plurality of individuals are simultaneously subjected to the same immunocompromising means, the degree of decrease, following a transient increase, in the average weight of the plurality of individuals may be used as an indicator for determination of immunocompromise.

As the immunosuppressive agent, it is preferable to use an immunosuppressive agent such as cyclosporin, tacrolimus, or ISP-1 that is used for the purpose of suppressing an immunological rejection reaction at the time of an organ transplant, etc., or a steroid such as methylprednisolone that exhibits immunosuppression as a side effect. They are all commercially available and can be purchased and used, preferred examples including cyclosporin, tacrolimus, and a steroid such as methylprednisolone acetate; among the steroids methylprednisolone acetate is particularly preferable, and the commercial product Depo Melcort (Fuji Pharma Co., Ltd.) may be used.

From the viewpoint of sufficient immunocompromise and prevention of excessive animal debilitation, it is necessary to set the amount of immunosuppressive agent administered to an animal by appropriately adjusting it while examining the above-mentioned indicator for determination of immunocompromise and the effects on the animal that accompany immunocompromise, such as food intake by the animal.

For example, the amount of methylprednisolone acetate administered in one dose is preferably in the range of 0.1 to 100 mg/kg, and when the degree of immunocompromise and the burden on the animal are taken into consideration it is more preferably 1 to 10 mg/kg, and yet more preferably 2 to 5 mg/kg. Furthermore, the amount of cyclosporin administered in one dose is preferably in the range of 0.1 to 50 mg/kg, and when the degree of immunocompromise and the burden on the animal are taken into consideration it is more preferably 1 to 25 mg/kg, and yet more preferably 2 to 10 mg/kg. Moreover, the amount of tacrolimus administered in one dose is preferably in the range of 0.001 to 10 mg/kg, and when the degree of immunocompromise and the burden on the animal are taken into consideration it is more preferably 0.005 to 5 mg/kg, and yet more preferably 0.01 to 3 mg/kg.

Similarly, from the viewpoint of sufficient immunocompromise and prevention of excessive animal debilitation, it is necessary to set the number of times of administration of an immunosuppressive agent, the frequency of administration, and the period of administration by appropriate adjustment while examining the above-mentioned indicator for determining immunocompromise and the effects on the animal that accompany immunocompromise, such as food intake by the animal.

The number of times of administration may be single administration or repeated administration, but when the degree of immunocompromise and the burden on the animal are taken into consideration, administration is preferably repeated two or more times.

The frequency of administration is preferably once in 2 to 21 days, and when the burden on the animal and the evaluation period are taken into consideration it is more preferably once in 7 to 14 days.

The period of administration from the start of administration up to immunocompromise is preferably within 16 weeks, and when the burden on the animal and the evaluation period are taken into consideration it is more preferably within 6 weeks.

With regard to the administration method, oral administration, intravenous administration, percutaneous administration, intramuscular and subcutaneous administration, etc. can be cited as preferred examples, but from the viewpoint of reliability of administration, intramuscular injection, percutaneous administration, etc. are more preferable.

Specifically, for example, administration of methylprednisolone acetate may suitably be carried out with an amount administered in one dose of 2 to 4 mg/kg at an administration frequency of once in 7 to 14 days with a single administration or by administration repeated 2 to 6 times.

Furthermore, administration of cyclosporin may suitably be carried out with an amount administered in one dose of 2 to 10 mg/kg at an administration frequency of once in 1 to 14 days with a single administration or administration repeated 2 to 6 times.

Moreover, administration of tacrolimus may suitably be carried out with an amount administered in one dose of 0.01 to 3 mg/kg at an administration frequency of once in 1 to 14 days with a single administration or administration repeated 2 to 6 times.

Furthermore, for example, after methylprednisolone acetate is administered at 2 to 24 mg/kg, if the degree of decrease in weight following a transient increase is a decrease of 5% to 20% from the weight prior to administration, it is determined that the degree of immunocompromise is suitable for inoculation with the infecting microorganism.

Moreover, after cyclosporin is administered at 2 to 60 mg/kg, if the degree of decrease in weight following a transient increase is a decrease of 5% to 20% from the weight prior to administration, it is determined that the degree of immunocompromise is suitable for inoculation with the infecting microorganism.

Furthermore, after tacrolimus is administered at 0.01 to 18 mg/kg, if the degree of decrease in weight following a transient increase is a decrease of 5% to 20% from the weight prior to administration, it is determined that the degree of immunocompromise is suitable for inoculation with the infecting microorganism.

The nail of an animal and the infected animal model of the present invention are prepared by infecting with the superficial fungus an animal that has been subjected to the above-mentioned pretreatment, and in such infection, it is preferable to control the infection by the dose of the microorganism; specifically, a fungus with which infection is to be effected is cultured in advance in a standard agar medium, this is scraped off with a platinum spatula, the fungal cells themselves or part of the fungal cells such as the conidia are taken out, they are added to physiological saline, a fungal liquid is prepared at $1 \times 10^7$ to $1 \times 10^9$ conidia/mL, and a nonionic surfactant such as, for example, Triton X or Tween 80 (Wako Pure Chemical Industries, Ltd.) is preferably added at 0.01% to 0.1% in order to enhance the dispersibility of the fungal cells or said part thereof. 10 to 1000 μL of this fungal liquid is administered to the nail of an animal that has been subjected to the above-mentioned compromising of immunocompetence. The amount of fungal liquid administered is adjusted in accordance with the dimensions of the site of administration, and when administration is carried out for the nail of a rabbit or a guinea pig, 100 to 500 μL can be cited as a suitable example.

As a method for inoculating with the fungal liquid, coating the surface or subcutaneous injection can be cited as examples, and in terms of a target nail being reliably inoculated and simplicity of operation, direct coating of the nail surface is preferable. With regard to the site that is coated with the fungal liquid, in addition to a target nail, coating the tissue around the nail is also effective in terms of reliably establishing infection in a short period of time. For example, by coating not only the nail plate but also the lateral nail fold, the proximal nail fold, and the eponychium (cuticle), which are present on the border between the nail and the skin, it is possible to sufficiently infect not only the nail plate side but also the nail bed side in a short period of time since the fungus can enter well from the lateral side of the nail.

With regard to the infection period during which a target tissue is inoculated with an infection-causing microorganism and the microorganism is grown, it is typically 1 to 16 weeks, and when the burden on the animal and the evaluation period are taken into consideration the infection period is preferably 2 to 6 weeks. Such infection may be carried out in an open system, but in order to prevent contamination by microorganisms and improve the homogeneity of infection, it is useful to carry out the infection in a sealed state. As such a sealed method, for example, a commercial patch plaster, a bandage, etc. may be used. Furthermore, instead of a patch plaster, infection may be carried out by enclosing using a finger stall. When enclosing using a finger stall, etc., it is preferable to maintain a wet state by appropriately supplying moisture to an affected part since infection is promoted.

Furthermore, after carrying out growth in a sealed state for a fixed period of time, the finger stall, etc. is removed to make an open state, and the fungus may be grown continuously in the tissue in a state where it is left standing. As a period for which it is left standing, 1 to 8 weeks can be cited as a desirable example, but when the burden on the animal and the evaluation period are taken into consideration, 2 to 6 weeks is preferable.

By appropriate adjustment and combination of the above-mentioned infection period and period left standing to thus control the infected site and infection intensity by a fungus within the nail, it is possible to prepare various infected nails.

In such an infection step, the end point thereof is determined by examining the change in state of the site infected by the infection. As indicators for completion of the infection, the fungus being uniformly distributed in the infected site and properties that are different from an uninfected site being exhibited are used. In the case of onychomycosis, it can be determined that the infection is completed when yellowish white cloudiness of the nail spreads throughout the nail. It is of course possible to determine the degree of infection by examining using a microscope or a magnifier and visually checking the growth state or the number of cells in the tissue, or sampling part of the tissue, sowing it on a medium, and examining the growth of the cells therein.

In the present invention, after carrying out infection by inoculation of the nail with a fungus, a thin section sample of the nail is prepared and subjected to PAS (Periodic acid Schiff stain) staining, and by analyzing an optical microscope photographic image of the stained thin section sample the proportion of the stained portion area relative to the cross-sectional area of the nail may be calculated as a percentage.

As a specific method for thin sectioning of a sample, for example, an animal that has been subjected to the above-mentioned infection operations is euthanized under anesthesia, a finger part containing the nail is cut and collected, placed in a formalin solution (Mildform 20 N, Wako Pure Chemical Industries, Ltd.) and fixed, and subsequently decalcification and neutralization treatments and paraffin embedding are carried out. This sample is thinly sliced into a thickness of on the order of 6 to 8 μm by a sliding microtome (LS-3, Yamato Kohki Industrial Co., Ltd.), adhered to a slide glass by tape, and allowed to stand for 5 minutes or longer, following this UV rays are applied thereto using a UV irradiator (Tokyo Instruments Inc.) for 3 to 5 minutes, the sample is subsequently immersed in TPC liquid (Tokyo Instruments Inc.), and the tape is peeled off, this being a desirable example of the method.

As a specific method for PAS staining, for example, the above-mentioned thin section sample is washed with xylene and ethanol so as to remove paraffin, and washed with water. This sample is subjected to an oxidation treatment using periodic acid solution (Muto Pure Chemicals Co., Ltd.) for 15 minutes, washed with running water for 3 minutes, and then stained with Schiff reagent (Muto Pure Chemicals Co., Ltd.) for 15 minutes. It is further treated with aqueous nitrous acid (Muto Pure Chemicals Co., Ltd.) for 5 minutes twice and washed with running water for 3 minutes. Subsequently, it is stained using Mayer's hematoxylin solution (Wako Pure Chemical Industries, Ltd.) for 40 seconds, and color is brought out with running water for 15 minutes. After water is removed using ethanol, clearing using Lemosol (Wako Pure Chemical Industries, Ltd.) is carried out for 3 minutes three times, and sealing using Softmount (Wako Pure Chemical Industries, Ltd.) and a cover glass is carried out, this being a desirable example of the method.

As a specific method for image analysis, for example, the nail sample after the above-mentioned thin slicing and PAS staining operations is photographed using an optical microscope at a magnification of 40 to 400 times, an image thereof is taken into computer software for image analysis, an entire cross-section of the nail in the image is identified in the software, and a stained portion and an unstained portion within the region are differentiated by binarization. The threshold value for binarization is set at an optimum value that can differentiate fungal cells from the nail tissue most accurately while checking the histopathological image for each sample. By individually calculating the area of the entire cross-section of the nail and the area of the stained portion, the proportion of the stained portion area relative to the cross-sectional area of the nail is determined as a percentage, this being a desirable example of the method.

Furthermore, as a specific method for determining that more stained portion is present in the lower half, in the depth direction, of the nail than in the upper half, for example, a method in which a photograph is taken using an optical microscope at a magnification of 40 to 400 times and subjected to simple visual evaluation to thus determine whether there is more or less stained portion in the lower half on the nail bed side or the upper half on the nail plate side, or a method in which in the same manner as above a photographed image is taken into computer software for image analysis, the cross-section of the nail is specified by equally dividing the image into two in the depth direction in the software, stained portions and unstained portions within the regions of the lower half on the nail bed side and the upper half on the nail plate side are differentiated by binarization, and the areas of the stained portions of the two halves are compared can be suitably cited.

The infected nail of an animal and the infected animal model of the present invention, which are prepared by the above-mentioned procedure, have similar symptoms to those of an intractable infectious disease in humans. A test material is administered to such an infected nail and an infected animal model, the process via which an infected site becomes similar to a normal site is examined, and the antifungal action, etc. of the test material toward onychomycosis can thus be determined; they are therefore very useful in an evaluation method for a drug for the treatment of onychomycosis. That is, when comparing a case in which a test material is administered to the infected nail of an animal and the infected animal model of the present invention with a case where it is not administered, when a return to the normal state is shown in the case of administration and a return to the normal state is not shown in the case of non-administration, it can be determined that the test material has efficacy toward onychomycosis. Furthermore, when two types of test materials are also tested in the same manner, and one thereof shows a higher probability for the degree of return to the normal state, it can be determined that said test material has a better antifungal treatment effect toward onychomycosis than the other. Furthermore, by changing the amount of test material administered and examining the responsiveness thereto, the concentration dependence of the antifungal effect of the test material can be determined.

When carrying out such determination, by collecting part of a treated site and examining the change in form of the cells by electron microscope or by sowing it on a medium, etc. and examining the degree of growth of the surviving cells as an indicator, it is possible to determine that the effect of the test material is low when the degree of growth is high and the effect of the test material is high when the degree of growth is low. In this case, determination of the degree of growth may be carried out by separately preparing in advance a calibration curve of number of conidia—colony area from data obtained by changing the number of conidia sown, measuring the colony area obtained as a result of culturing, estimating viable cells that survive in part of the sown treatment site as the number of conidia using the above calibration curve, and determining that the lower the number of conidia estimated, the higher the antifungal effect exhibited by the test material. In such a determination, antifungal effects can be compared quantitatively. Furthermore, it is preferable for the medium used for sowing to contain in advance 0.1 to 10 mass % of a phospholipid and 0.1 to 10 mass % of a nonionic surfactant such as 'Tween 80', thus inactivating surviving test material and reducing the noise. In accordance with such determination, the effect of a test material can be compared quantitatively. In particular, in an intractable infectious disease such as onychomycosis, since complete recovery in a short period of time is rare, the estimated number of viable cells is an important point for evaluation of the effect. This is because the antifungal effect can be compared in an incompletely cured state.

In other intractable infectious diseases, the same procedure as for onychomycosis above is carried out, an infected nail and an infected animal model are prepared, and the treatment effect can be understood quantitatively by examining the process of curing of the infection by administration of a test material.

EXAMPLES

The present invention is explained below in further detail by reference to Examples, but the present invention is not limited by these Examples and may be modified in a variety of ways as long as the modifications do not depart from the technical scope of the present invention.

Example 1

(Rabbit Immunity Suppression)

Figure 1:
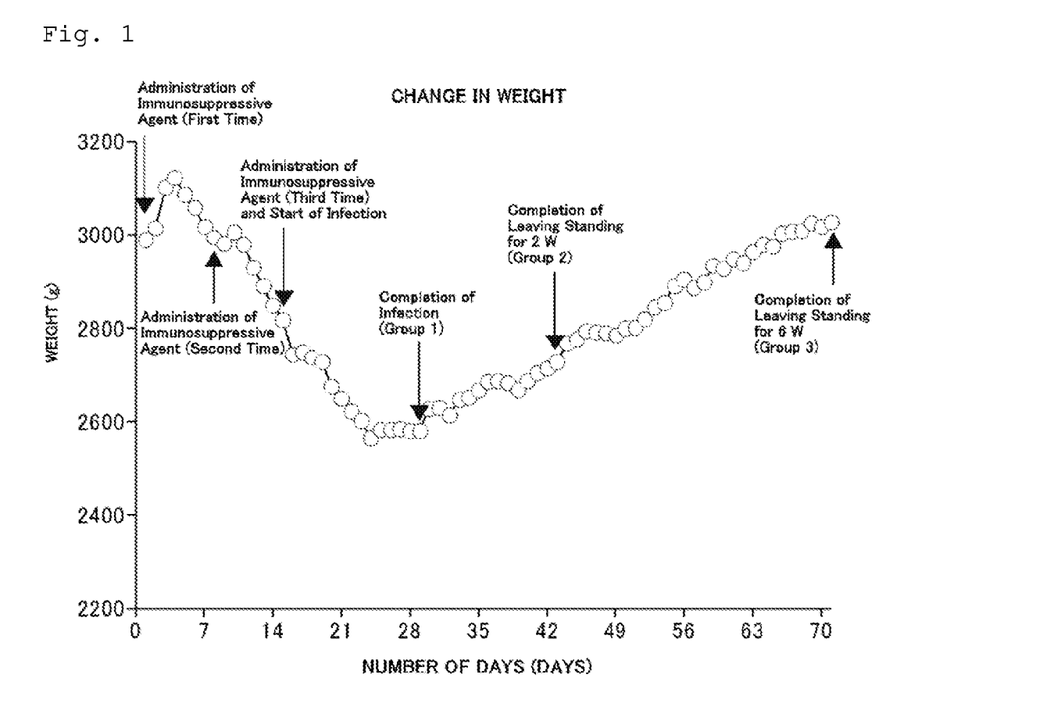
FIG. 1 A diagram showing change in weight of rabbits after administration of an immunosuppressive agent in Example 1.

14 week old Japanese white rabbits (Kbl: JW, Kitayama Labes Co., Ltd.) were quarantined and acclimatized for 1 week. After acclimatization, a long-acting methylprednisolone acetate preparation (Depo Melcort, Fuji Pharma Co., Ltd.) was administered as an immunosuppressive agent to femoral muscle a total of three times, with 4 mg/kg as the amount administered in one dose, at intervals of once a week. The weight of individual rabbits after administration of the immunosuppressive agent was measured, and it was confirmed that due to immunocompromise after administration of the immunosuppressive agent the weight transiently increased and subsequently decreased. At a point 2 weeks after starting the administration, at which the average of the weights of a total of 15 rabbits had decreased by about 6% from the weight prior to administration, inoculation with a fungal liquid was carried out. The change in average weight of the total of 15 rabbits is shown in FIG. 1.

(Preparation of Fungal Liquid)

*Trichophyton mentagrophytes* stored at 4° C. was added to 1.5 mL of physiological saline in a safety cabinet, thus preparing a fungal suspension. 300 mL of water was added to 1.8 g of Sabouraud's medium (FLUID SABOURAUD MEDIUM) and 4.5 g of agar (Bacto Agar), and after stirring the mixture was sterilized using an autoclave and allowed to stand on an inclined stage, thus preparing a slant medium. The fungal suspension was added to the medium and cultured at 28° C. Part of the fungus thus cultured was collected and added to 2 to 20 mL of a solution containing 0.05% of Tween 80 (Wako Pure Chemical Industries, Ltd.). The concentration of the fungal conidial liquid was measured using a hemocytometer (Erma Inc.), and preparation was carried out so as to give $1.1 \times 10^8$ to $1.3 \times 10^8$ conidia/mL. The amount of Tween 80 solution was adjusted, and $1.0 \times 10^8$ conidia/mL was finally used for the infection experiment.

(Infected Rabbit Model)

The rabbits (Japanese white rabbit) that had been subjected to the above-mentioned immunocompromise were locally anesthetized, 200 μL of the fungal liquid prepared above was coated on the nail cuticle portion and a gauze, and the rabbit nail was covered with the gauze, which was fixed by tape. Furthermore, a finger stall was fitted on the rabbit finger, and a hole was made for dripping water for wetting. Following this, the condition of the rabbit and the state of dryness of the nail portion were checked every day for 2 weeks, and when dryness of the nail was observed, purified water was dripped on to wet it.

In addition to the infected rabbit model that had been subjected to the above-mentioned 2 week infection operations, infected rabbit models for which, after the 2 week infection operations, the finger stall, etc. were removed and they were left standing for a further 2 weeks or a further 6 weeks without any operations being carried out were prepared. They were defined as Group 1, Group 2, and Group 3 respectively.

(Thin Sectioning of Sample)

The rabbits of Group 1 to Group 3 above were euthanized under anesthesia, and finger parts containing the nail were cut and collected, placed in formalin solution (Mildform 20 N, Wako Pure Chemical Industries, Ltd.), and fixed. Subsequently, decalcification and neutralization treatments were carried out, and paraffin embedding was carried out by placing the finger in an embedding dish, pouring paraffin thereinto, and solidifying by cooling. This was thinly sliced into a thickness of on the order of 6 μm by a sliding microtome (LS-113, Yamato Kohki Industrial Co., Ltd.), adhered to a slide glass by tape, and allowed to stand for 5 minutes or longer. Following this, UV rays were applied thereto using a UV irradiator (Tokyo Instruments Inc.) for 2 minutes, the sample was subsequently immersed in TPC liquid (Tokyo Instruments Inc.), and the tape was peeled off.

(Staining of Sample)

The above-mentioned thin section sample was washed with xylene and ethanol so as to remove paraffin, and washed with water. This sample was subjected to an oxidation treatment using periodic acid solution (Muto Pure Chemicals Co., Ltd.) for 15 minutes, washed with running water for 3 minutes, and stained with Schiff reagent (Muto Pure Chemicals Co., Ltd.) for 15 minutes. It was further treated with aqueous nitrous acid (Muto Pure Chemicals Co., Ltd.) for 5 minutes twice and washed with running water for 3 minutes. It was stained using Mayer's hematoxylin solution (Wako Pure Chemical Industries, Ltd.) for 40 seconds, and color was brought out with running water for 15 minutes. After water was removed using ethanol, clearing using Lemosol (Wako Pure Chemical Industries, Ltd.) was carried out for 3 minutes three times, and sealing using Softmount (Wako Pure Chemical Industries, Ltd.) and a cover glass was carried out.

(Measurement of Area of Stained Portion)

An entire image of the nail tissue sample after the above-mentioned PAS staining operations was photographed using an optical microscope at a magnification of 100 times, this image was taken into Adobe Photoshop, an entire cross-section of the nail in the image was identified in the software, and the stained and unstained portions within the region were differentiated by binarization. The threshold value for binarization was set at an optimum value between 100 and 200 that could differentiate fungal cells from the nail tissue most accurately while checking the histopathological image for each sample. By calculating the area of the entire cross-section of the nail and the area of the stained portion, the proportion of the stained portion area relative to the cross-sectional area of the nail was determined as a percentage.

(Confirmation of Infection)

The above-mentioned stained sample was evaluated using an optical microscope based on the evaluation criteria shown in Table 1 below with evaluation scores of 0 (−) to 3 (+++). Evaluation was carried out for each of a total of six areas, that is, the upper half nail plate side and the lower half nail bed side in the nail depth direction for each of the extremity side, the middle part, and the nail matrix side, for which the nail was divided equally into three along the longer diameter direction.

TABLE 1

Evaluation criteria for confirmation of infection

| Infection intensity | Evaluation | Determination criteria |
|---|---|---|
| No infection | 0 (−) | No infection (PAS positive cells) at all. |
| Light degree of infection | 1 (+) | PAS positive cells were clearly observed, but PAS-stained sites were localized. |
| Medium degree of infection | 2 (++) | More PAS positive cells were observed than in light degree of infection, widely PAS-stained sites were observed in at least two separate sites. |
| Serious degree of infection | 3 (+++) | Very many PAS positive cells were observed, conditions were more serious than medium degree of infection, and PAS-stained sites were observed over almost the entire region. |

With respect to each of 29 to 30 nails (6 nails×5 animals) of the infected rabbit models of Group 1 to Group 3 of Example 1, the area of the stained portion of the entire nail tissue sample was measured. The measurement results are shown in Table 1.

TABLE 2

Results of measurement of area of stained
portion (average value, n = 29 to 30)

| Name of group | Group 1 | Group 2 | Group 3 |
|---|---|---|---|
| Stained area proportion (%) | 4.0% | 4.5% | 7.9% |

Group 1: group with 2 weeks infection (30 nails)
Group 2: group with 2 weeks infection + leaving standing for 2 weeks (29 nails)
Group 3: group with 2 weeks infection + leaving standing for 6 weeks (30 nails)

Furthermore, with respect to each of 29 to 30 nails (6 nails×5 animals) of the infected rabbit models of Group 1 to Group 3 of Example 1, infection was checked for the above-mentioned total of six sites. Table 3 shows the infection rate for each site, obtained by expressing as a percentage the value obtained by dividing the number of infection-positive sites with infection of an evaluation score of 1 (+) or greater by the number of sites checked (29 to 30 nails).

[Table 3]

TABLE 3

Infection rates for different sites

| Group | Site | Extremity side | Middle part | Nail matrix side |
|---|---|---|---|---|
| Group 1 | Nail plate side | 0.0% (0/30 nails) | 6.7% (2/30 nails) | 46.7% (14/30 nails) |
|  | Nail bed side | 13.3% (4/30 nails) | 23.3% (7/30 nails) | 36.7% (11/30 nails) |
| Group 2 | Nail plate side | 0.0% (0/29 nails) | 17.2% (5/29 nails) | 43.3% (13/30 nails) |
|  | Nail bed side | 62.1% (18/29 nails) | 37.9% (11/29 nails) | 30.0% (9/30 nails) |
| Group 3 | Nail plate side | 40.0% (12/30 nails) | 50.0% (15/30 nails) | 20.0% (6/30 nails) |
|  | Nail bed side | 90.0% (27/30 nails) | 46.7% (14/30 nails) | 13.3% (4/30 nails) |

Figure 2:
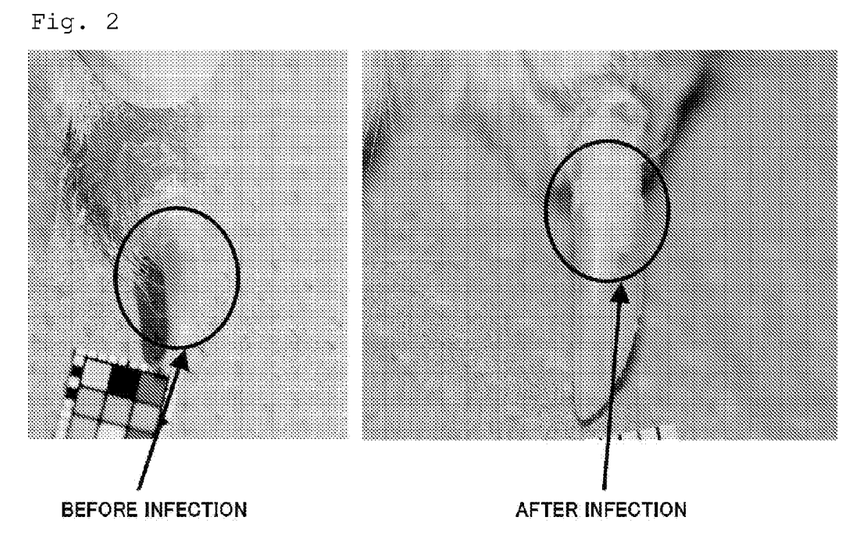
FIG. 2 A photographic diagram showing the state of the nail of a rabbit of Group 2 of Example 1 before and after superficial fungal infection.

Group 1: group with 2 weeks infection
Group 2: group with 2 weeks infection + leaving standing for 2 weeks standing
Group 3: group with 2 weeks infection + leaving standing for 6 weeks standing Furthermore, FIG. 2 shows a photograph of the state of the nail of a rabbit of Group 2 of Example 1 before and after superficial fungal infection. In FIG. 2, the part circled in the picture on the left is not infected and has a trace of redness, but the part circled in the picture on the right is cloudy and has no redness. This cloudiness indicates infection with fungus.

Figure 3:
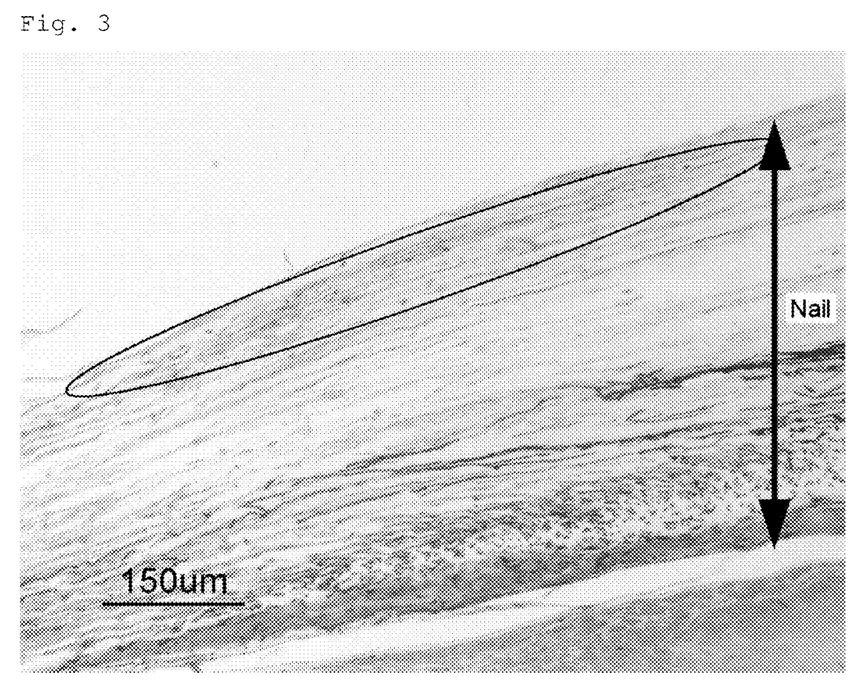
FIG. 3 A histopathological photographic diagram of the nail bed side middle part of the nail of a rabbit of Group 2 of Example 1 after superficial fungal infection.

Moreover, FIG. 3 shows a photograph by optical microscope at a magnification of 40 times of a sample obtained by staining the nail bed side middle part of the nail of a rabbit of Group 2 of Example 1 after superficial fungal infection. In FIG. 3, the part shown by the arrow is the nail portion and the part that is stained violet by PAS staining is the mycelium, indicating that there is fungal infection widely in the nail. The circled part was particularly markedly infected.

Figure 4:
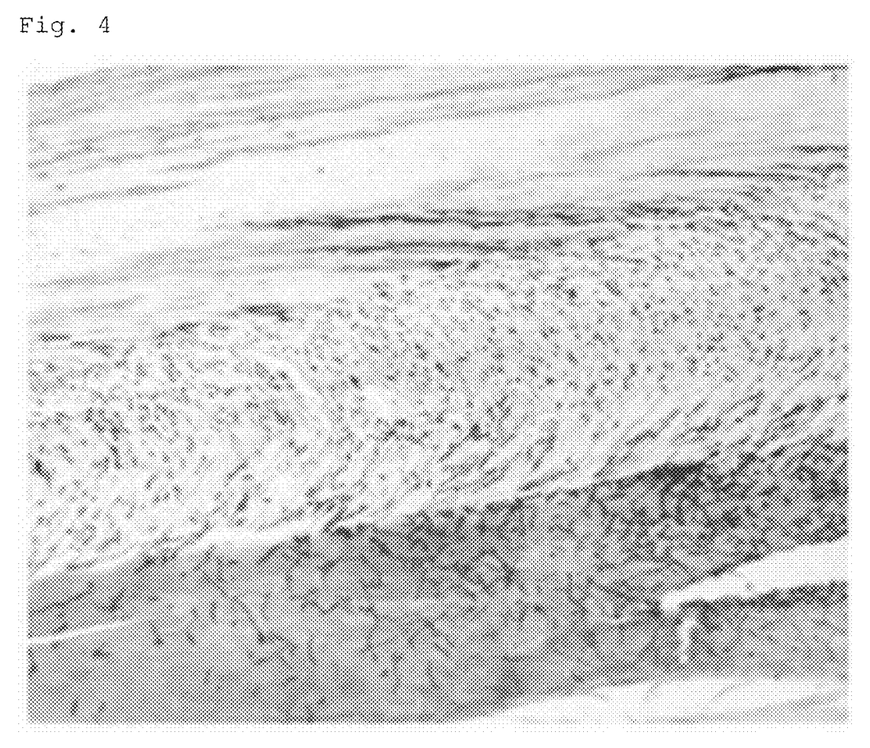
FIG. 4 A histopathological photographic diagram of the nail bed side middle part of the nail of a rabbit of Group 3 of Example 1 after superficial fungal infection.

Furthermore, FIG. 4 shows a photograph by optical microscope at a magnification of 100 times of a stained sample of the nail bed side middle part of the nail of a rabbit of Group 3 of Example 1 after superficial fungal infection. The part that is stained violet by PAS staining is the mycelium, indicating that all the layers of the nail are infected with fungus.

Figure 5:
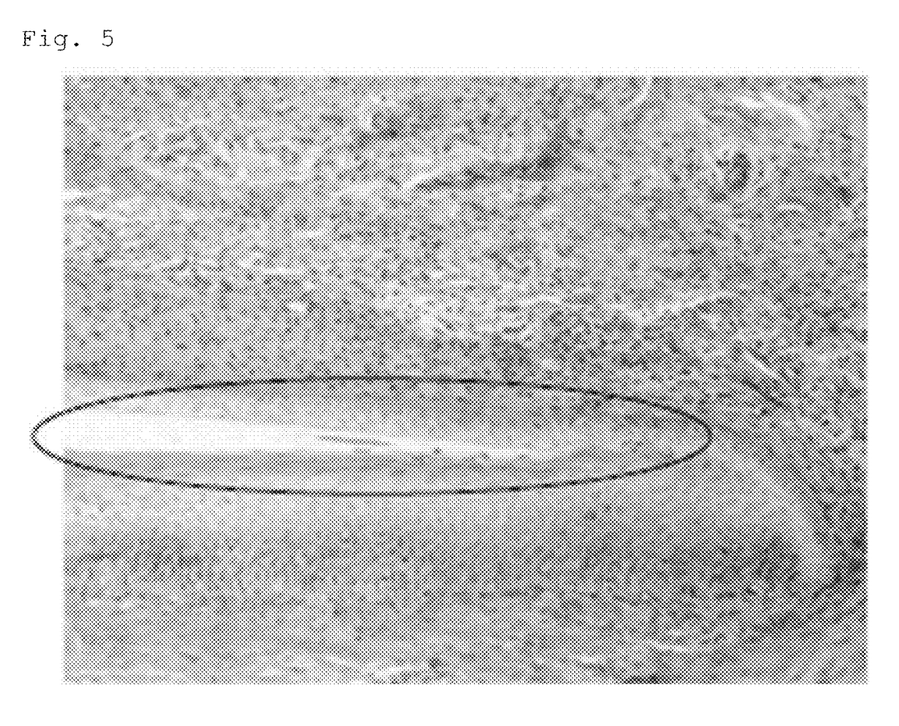
FIG. 5 A histopathological photographic diagram of the nail bed side middle part of the nail of a rabbit of Group 2 of Example 1 after superficial fungal infection.

Moreover, FIG. 5 shows a photograph by optical microscope at a magnification of 100 times of a stained sample of the nail bed side middle part of the nail of a rabbit of Group 2 of Example 1 after superficial fungal infection. The part that is stained violet by PAS staining is the mycelium, indicating that there is a marked fungal infection.

From the results in Table 2 above and FIGS. 3 to 5, it can be seen that an infected nail model for which the proportion of the stained portion area relative to the cross-sectional area of the nail is 4% or greater, that is, the proportion of the area occupied by fungal cells is 4% or greater, the interior of the nail is sufficiently infected with a fungus, analysis of a fungal infection is easy, and use in an accurate evaluation of an antifungal agent is possible can be prepared in a short period of time, that is, 4 to 10 weeks after administration of an immunosuppressive agent.

Furthermore, from the results in Table 3 above and FIGS. 3 to 5, it can be seen that infection with a superficial fungus is observed across almost all the nail and, in particular, within the nail overall more fungus infiltrates into the nail bed side, which is a deep part of the nail, than the nail plate side. Moreover, from the result of Table 3, more fungal infection is observed on the nail matrix side in Group 1, in all regions on the nail matrix side and on the nail bed side in Group 2, and on the extremity side and in the middle part in Group 3; it can be seen that a nail infection model is obtained for which, by providing a period in which it is left standing, the site with a high infection rate shifts and more fungus infects a specific site such as the nail extremity side or the nail matrix side.

From the above results it is confirmed that, although it is said that the nail is blocked from the bloodstream and no immune system cells are present therein, in accordance with infection by inoculation with a superficial fungus after compromising immunity by administering an immunosuppressive steroid, it is possible to prepare in a short period of time a superficial fungal infection model of the nail for which the infection rate is high, a fungus sufficiently infiltrates into the nail bed side, which is a deep part of the nail, reproducibility is good, and clinical manifestation is reflected, which is conventionally impossible to prepare.

The invention claimed is:

1. A method for preparing an infected nail which is infected with a superficial fungus, comprising:
   compromising immunity of an experimental animal by administering an immunosuppressive agent;
   inoculating a nail of the experimental animal with the superficial fungus to infect the nail of the experimental animal, wherein the inoculated nail is enclosed by a finger stall to maintain a wet state of the inoculated nail; and
   isolating the inoculated nail from the experimental animal, wherein the experimental animal's weight in the inoculating step is decreased by 1%-30% from the weight prior to the administration of the immunosuppressive agent, wherein the fungal cells are present in the nail extremity side, the nail middle part and the nail matrix side of each the nail plate side and the nail bed side, wherein the proportion of the area occupied by the fungal cells relative to the overall cross-section area of the inoculated nail is between 4% and 7.9%, and wherein the fungal cells are present more in bed side of the inoculated nail than in the nail plate side of the inoculated nail.

2. The method according to claim 1, wherein the superficial fungus is one or more types selected from the group consisting of *Trichophyton mentagrophytes, Trichophyton rubrum, Trichophyton violaceum, Trichophyton verrucosum, Trichophyton tonsurans, Microsporum canis, Microsporum gypseum, Epidermophyton floccosum, Hortaea werneckii, Alternaria alternata, Aspergillus fumigatus, Aspergillus flavus, Aspergillus terreus, Paecilomyces lilacinus, Fusarium solani, Scopulariopsis brevicaulis, Candida albicans, Candida tropicalis, Candida parapsilosis, Candida glabrata, Cryptococcus neoformans,* and *Trichosporon asahii.*

3. The method according to claim 2, wherein the superficial fungus is *Trichophyton mentagrophytes.*

4. The method according to claim 1, wherein the experimental animal is selected from the group consisting of rabbit, guinea pig, rat, dog, and monkey.

5. The method according to claim 1, wherein the experimental animal's weight in the inoculating step is decreased by 3%-30% from the weight prior to the administration of the immunosuppressive agent.

* * * * *